(12) United States Patent
Pokorney et al.

(10) Patent No.: US 8,337,446 B2
(45) Date of Patent: Dec. 25, 2012

(54) PROSTHETIC HEART VALVE HOUSING

(76) Inventors: James L. Pokorney, Northfield, MN (US); Kemal Schankereli, Stillwater, MN (US)

(*) Notice: Subject to any disclaimer, the term of this patent is extended or adjusted under 35 U.S.C. 154(b) by 585 days.

(21) Appl. No.: 11/514,792

(22) Filed: Sep. 1, 2006

(65) Prior Publication Data
US 2007/0055357 A1 Mar. 8, 2007

Related U.S. Application Data

(60) Provisional application No. 60/713,874, filed on Sep. 2, 2005, provisional application No. 60/818,661, filed on Jul. 5, 2006.

(51) Int. Cl.
*A61M 5/00* (2006.01)
(52) U.S. Cl. .......................................................... 604/9
(58) Field of Classification Search ........................ None
See application file for complete search history.

(56) References Cited

U.S. PATENT DOCUMENTS

| | | | | |
|---|---|---|---|---|
| 3,766,567 A | * | 10/1973 | Kahn et al. | 623/3.21 |
| 4,104,005 A | * | 8/1978 | Poirier | 417/394 |
| 4,118,806 A | * | 10/1978 | Porier et al. | 623/1.26 |
| 4,131,604 A | * | 12/1978 | Szycher | 528/79 |
| 4,434,811 A | * | 3/1984 | Murdoch | 137/515 |
| 5,269,764 A | * | 12/1993 | Vetter et al. | 604/167.04 |
| 5,326,373 A | * | 7/1994 | Nagase | 623/3.26 |
| 5,685,700 A | * | 11/1997 | Izraelev | 417/423.7 |
| 6,001,056 A | | 12/1999 | Jassawalla et al. | |
| 6,346,071 B1 | * | 2/2002 | Mussivand | 600/16 |
| 2004/0054251 A1 | * | 3/2004 | Liotta | 600/17 |
| 2004/0162608 A1 | | 8/2004 | Haverich | |
| 2004/0231856 A1 | * | 11/2004 | Dallas et al. | 166/379 |
| 2006/0074271 A1 | * | 4/2006 | Cotter | 600/16 |

FOREIGN PATENT DOCUMENTS

JP 04220263 * 8/1992

* cited by examiner

*Primary Examiner* — Christopher D Koharski
*Assistant Examiner* — Rebecca Straszheim
(74) *Attorney, Agent, or Firm* — Oppenheimer Wolff Donnelly; Adam Kiedrowski; Barbara A. Wrigley

(57) ABSTRACT

A housing for a prosthetic valve comprises a first housing portion having a conduit end opening and a valve end opening, a second housing portion having a conduit end opening, a valve end opening and a threaded outer surface adjacent the valve end opening, a first conduit coupled to the conduit end opening of the first housing portion, a second conduit coupled to the conduit end opening of the second housing portion, and a connecting member having a threaded inner surface. The threaded outer surface of the second housing portion is structured to mate with the threaded inner surface of the connecting member to couple the first housing portion to the second housing portion.

7 Claims, 3 Drawing Sheets

PROSTHETIC HEART VALVE HOUSING

This application claims priority from provisional patent application U.S. Ser. No. 60/713,874 filed 2005 Sep. 2 and provisional patent application 60/818,661 filed 2006 Jul. 5 (pages 13-15).

BACKGROUND—FIELD OF INVENTION

This invention relates to an improved prosthetic heart valve housing adopted for use with a prosthetic heart valve such that a prosthetic heart valve can be installed into the prosthetic heart valve housing at the time of implantation.

BACKGROUND—Applicant Patent Application 20050149093

A less invasive means invented by applicant to implant a prosthetic heart valve housing is described in U.S. Patent Application 20050149093 which is hereby incorporated by reference in its entirety. This invention relates to an implant, implant tools, and an implant technique for the interposition of an extracardiac conduit between the left ventricle of a beating heart and the aorta to form an alternative one-way blood pathway thereby bypassing the native diseased aortic valve.

The valve bypass graft described in this previous patent application consists of a hollow conduit having a first end opening, a second end opening, and a one-way valve located between the end openings. The valve is biased to allow one-way flow from the second end opening to the first end opening. A first slit opening is located between the first end opening and the valve and a second slit opening is located between the second end opening and the heart valve.

The implant tools consist of a vessel wall cutting tool and a heart wall piercing and dilating tool. The vessel wall cutting tool is sized to closely fit through the implant's first slit opening and the first end opening. The heart wall piercing and dilating tool is sized to closely fit through the implant's second slit opening and the second end opening.

The implant technique allows the surgeon to safely connect the implant between a heart chamber and a blood vessel without stopping the heart or impeding flow in the blood vessel.

Although this prior invention provides key enabling technologies that will allow mainstream use of the valve bypass graft procedure, an improved valve housing design is needed to make the procedure safer and more effective. In the new invention described herein, the prosthetic heart valve is intended to be installed into the prosthetic heart valve housing by the user at the time of implantation.

OBJECTS AND ADVANTAGES

The primary object of the present invention is to provide an improved prosthetic heart valve housing adopted for use with a prosthetic heart valve that can be installed into the prosthetic heart valve housing at the time of implantation.

Specifically, the invention has the following advantages:

This invention encourages the use the most appropriate available prosthetic heart valve by allowing a surgeon, at the time of implantation, to select for installation into the prosthetic heart valve housing a prosthetic heart valve having a proven long term performance history. This invention allows a surgeon to install the selected prosthetic valve into the prosthetic heart valve housing without altering or modifying the valve in anyway.

This invention simplifies the prosthetic valve installation by eliminating the need for suturing the valve to the adjoining conduits.

This invention maximizes blood flow through the implant by allowing a surgeon to select a prosthetic valve that is larger in diameter than the conduits connected to the heart and blood vessel.

The invention minimizes the risks associated with a subsequent valve replacement procedure by allowing the implanted prosthetic valve to be easily removed and replaced.

The invention simplifies the valve bypass graft procedure by allowing any necessary implantation tool to be inserted and removed though the valve bypass graft without the need for a pre-cut slit through the graft.

The invention minimizes adverse tissue healing response or adverse blood interaction with the implant by providing a common blood contacting surface throughout the device.

The above mentioned objects and advantages of this invention will become apparent from the following description taken in connection with the accompanying drawings, wherein is set forth by way of illustration and example, preferred embodiments of this invention.

DESCRIPTION OF DRAWING FIGURES

GENERAL SUMMARY OF INVENTION

Figure 1:
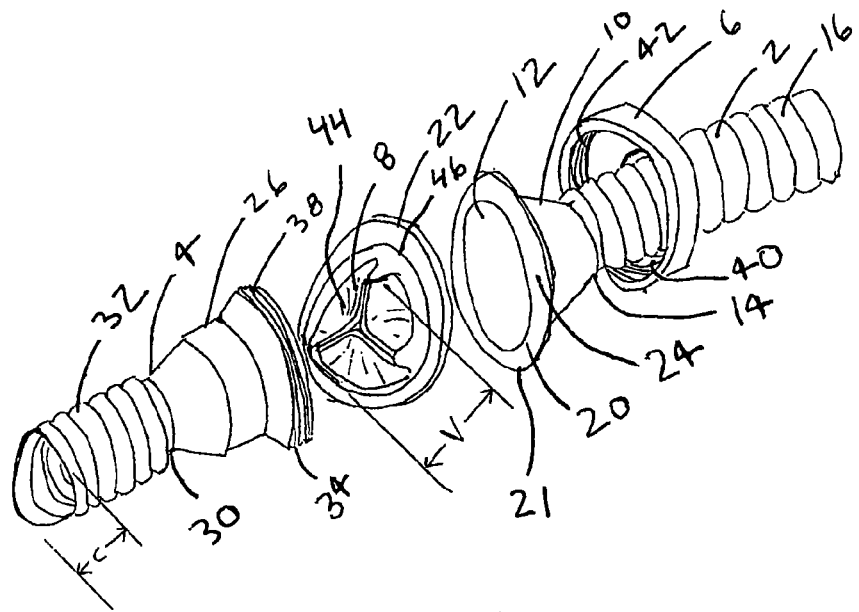
FIG. 1 is a perspective view of a prosthetic heart valve and a disassembled prosthetic heart valve housing.

The present invention provides a prosthetic heart valve housing adopted to allow blood flow. The prosthetic heart valve housing comprises an inlet conduit element, an inlet valve housing element, an outlet valve housing element, and an outlet conduit element. In use in a human body, a blood source, such as the heart, is attached to the inlet conduit element which is attached to the inlet valve housing element which is attached to the outlet valve housing element which is attached to the outlet conduit element which is attached to a blood sink, such as a blood vessel.

To allow only one-way blood flow through the prosthetic heart valve housing, the inlet and outlet valve housing elements of the prosthetic heart valve housing are adopted to hold a surgeon selected prosthetic heart valve. Prosthetic heart valves are of three general types: valves composed of processed human tissue, valves composed of processed animal tissue, or valves composed of a synthetic material such as carbon, polyurethane, titanium or some other suitable biomaterial. One element common to many of these valve designs is an annular periphery surface, or cuff, or sealing gasket located around the periphery of the working valve. This periphery surface is generally composed of a flexible biocompatible material. Example materials are polyester or Teflon fabric. The periphery surface, in conjunction with sutures inserted thru the periphery surface by a surgeon, is used to secure the valve into the heart annulus at the site of implantation to prevent leaks around the valve, thereby maintaining the one-way function of the valve.

When a prosthetic heart valve having such a periphery surface is installed by the surgeon into this new invention described herein, the valve's periphery surface provides 1) a seal between the valve housing elements that prevent leaks around the prosthetic valve, thereby maintaining the one-way function of the valve within the prosthetic heart valve housing and 2) a surface whereby the valve is retained and stabilized within the housing. The seal is made without using sutures or adhesives and can be completed in most cases in less than a minute, compared to twenty or more minutes required to install a valve into a conduit using sutures or adhesives.

Because of the high resistance to flow common to all prosthetic heart valves when compared to an open conduit of the same diameter, to maximize flow through the prosthetic heart valve housing the major internal diameter of the valve housing elements are larger than the minor internal diameters of both the outlet conduit element and the inlet conduit element.

The inlet and outlet valve housing elements may be formed of any suitable blood compatible material capable of containing blood and holding a prosthetic valve. For example, the housing elements could be composed of titanium, stainless steel, silicone, urethane, polycarbonate, polyester, Teflon, or any other suitable biomaterial. In a preferred embodiment, the housings are composed of titanium with the blood contacting surfaces lined with a thin polyester fabric.

The inlet and outlet conduit elements may be formed of any suitable blood compatible material capable of containing blood. For example, the conduit elements could be composed of silicone, urethane, polyester, Teflon, or any other suitable biomaterial. In a preferred embodiment, the conduits are composed of woven polyester fabric coated with collagen.

If found desirable, the housings and conduits could be combined to form one monolithic component. For instance, a combination component could be composed of a polyester fabric fabricated to have a larger diameter housing section and a smaller diameter conduit section.

In one embodiment, the outlet and inlet valve housing elements can be combined to form one element. In this design variation, a slot or opening is formed in the combined valve housing. The slot can provide tool access into either conduit. The slot also allows a prosthetic valve to be inserted and seated into the major internal diameter of the valve housing element. Once inserted, the slot is closed by suturing, applying adhesive, applying a clip or clamp or some other suitable means to form a blood tight seal preventing blood flow outside of the housing. The periphery surface of the prosthetic valve is held tightly against the internal surface of the valve housing by employing a preformed annular groove within the housing or applying adhesive, sutures, clips or some other suitable fastening means.

The conduit elements can be joined to the housing elements using various attachment methods. Attachment mechanism could be adhesive, welding, interference fits, annular threads, or any other suitable attachment mechanism. In one preferred embodiment, the attachment mechanism is a metal ring swaged over both elements forming a compressive radial seal.

After the prosthetic valve is installed within the prosthetic heart valve housing, the valve housing elements can be attached to each other using various attachment mechanisms. The attachment mechanism could be adhesive, welding, an interference fit, annular threads, or any other suitable attachment mechanism. To facilitate joining using any of these methods, the housing could be partially connected by using a hinge.

If the valve needs to be replaced due to failure or normal wear, an attachment mechanism that could be reversible, that is, easily opened again would be desirable. In one preferred embodiment, the attachment mechanism is a threaded nut adapted to compress and hold the periphery surface or cuff element of a prosthetic valve between the two housings. If required, this nut could be loosened at a later time to separate the housings to remove the prosthetic valve and replace with another valve.

In a preferred embodiment, the blood contacting surfaces of all the prosthetic heart valve housing elements are composed of the same biocompatible material or coating. It is known to those knowledgeable in the art that blood flow through unnatural man-made conduits can be problematic. The blood reacts badly to some foreign surfaces and causes excessive blood clotting, blood hemolysis, loose emboli, and or excessive deposition of pseudo-intima. The exact cause is not known, but it is known that some materials interact more passively with blood than others and that the transition from one man-made material to another, especially a transition from a metal to a textile surface, can be problematic. Based on this knowledge, it would be beneficial to design the prosthetic heart valve housing with the following two considerations in mind:

1. Use a good blood compatible material on all blood contacting surfaces,
2. Use the same material or class of material throughout; do not transition from one material to another because at that transition line blood interaction can be the most active.

A preferred design approach is to specify that the entire internal surface of the implant, from blood inlet (the ventricle) to blood outlet (the aorta) consist of one type of blood compatible surface. Since the prosthetic heart valve cuff is typically made of polyester or Teflon and conduit grafts are typically made of polyester or Teflon, the implant's blood contacting surfaces should be all polyester, all Teflon, or all some other similar biocompatible material. In one preferred embodiment, the conduits and the prosthetic valve cuff are all composed of polyester and the housings and the ventricle connector are composed of stainless steel. To minimize the transition issue between polyester and metal, the blood contacting surfaces of the metal components are covered with polyester fabric. In this invention, the connection of polyester elements is made outside the blood stream thereby eliminating a potential flow disturbance caused by exposed fabric edges. By designing the implant to have one continuous surface of polyester the problems associated with blood compatibility are minimized.

The implantation steps in a preferred embodiment are to attach the inlet conduit element to a blood source such as the apex of the left ventricle of a heart and to attach the outlet conduit element to a blood sink such as the descending aorta. After attachment, the conduits are temporarily occluded to allow a prosthetic heart valve to be installed within the outlet and inlet valve housing elements. The housings, in combination with a threaded nut, are adapted to capture and partially compress the periphery surface or cuff element of the prosthetic valve between the valve housing surfaces located near their major internal diameters. This intentional sandwiching of the cuff between the housings prevents blood flow around the periphery of the prosthetic valve thereby maintaining the one-way function of the valve. After the housings are joined, the temporarily occluded conduits are opened to allow one-way flow through the prosthetic heart valve housing/prosthetic valve assembly.

An important element of this invention is the variable diameter inherent in both housings, smaller near the conduit compared to larger near the valve. This variable diameter structure allows for the use of a prosthetic heart valve that is larger in diameter than the size of the conduits connected to the body. In prior art designs, the prosthetic valve selected for implant needed to fit within or between iso-diameteric conduits connected to it. Due to the obstructive elements inherent in all heart valve flow ways, a heart valve sized to fit an iso-diametric conduit would necessarily provide more resistance to flow than the same conduit alone. Therefore, to optimize blood flow through the conduits and valve, in this invention the valve is deliberately oversized to such a size that the restrictive nature of the valve obstructive elements is overtaken by the high flow nature of a larger valve. For example, a tissue valve labeled 25 mm in diameter is paired with a conduit or graft sized at 18 mm diameter.

Another important element of this invention is the annular surface design feature of each housing. The annular surface structure allows peripheral surfaces of a prosthetic heart valve to seat on the annular surfaces of the housings, thereby creating an efficient and simple seal among all three components.

The ability to insert a reliable and time-proven prosthetic heart valve into the housing assembly at the time of implant is also an important element of this design. A surgeon will be more comfortable using a valve bypass graft as a long term implant if he or she can efficiently and safely select and use an already proven reliable implant, especially a proven reliable tissue heart valve implant that needs to be stored in a liquid preservant before use.

Description of Invention Structure

Figure 2:
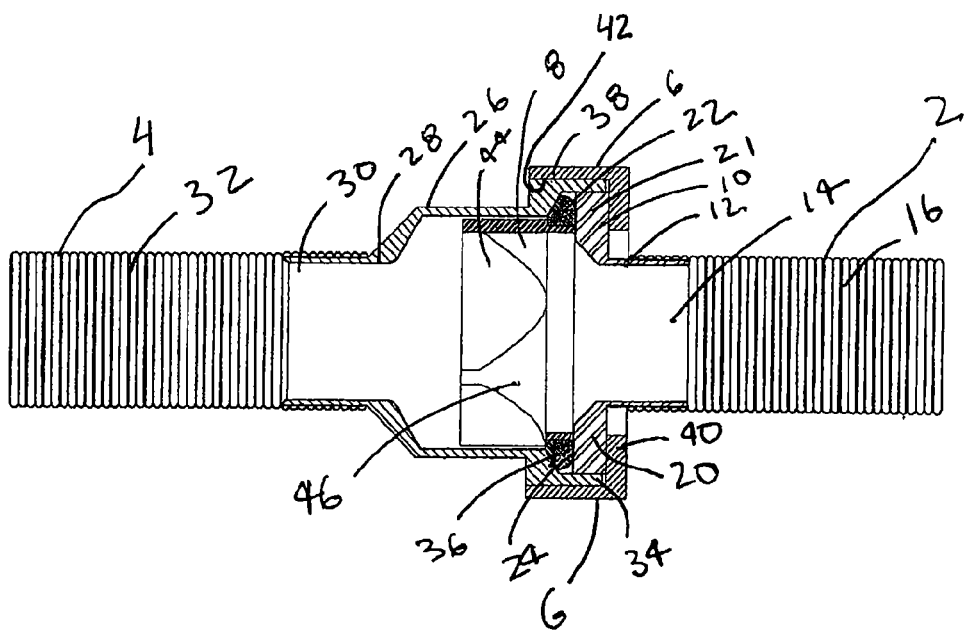
FIG. 2 shows a cross sectional view of a prosthetic heart valve installed within a prosthetic heart valve housing.

A preferred embodiment of the prosthetic heart valve housing is shown in FIGS. 1 and 2. The implant is comprised of three assemblies; a Ventricular Assembly 2, an Aortic Assembly 4, and a Connecting Locknut 6. The following is a more detailed description of each assembly and a general description of a Prosthetic Valve 8 contained within the Prosthetic heart valve housing.

The Ventricular Assembly 2 is composed of a Ventricular Valve Housing 10 composed of titanium and a Ventricular Housing Liner 12 composed of polyester fabric. The Ventricular Housing Liner 12 covers the blood contacting internal surfaces of the Ventricular Valve Housing 10. A Conduit End Opening 14 of Ventricular Valve Housing 10 is sized to accept a Ventricular Conduit 16. A Valve End Opening 20 of Ventricular Valve Housing 10 is configured with an Annular Surface 24 to mate with Periphery Surface 22 of Prosthetic Valve 8. The Valve End Opening 20 is larger than the Conduit End Opening 14. Near the Valve End Opening 20 is a Flange 21.

The Aortic Assembly 4 is similar in general design to the Ventricular Housing 2. Specifically, the Aortic Assembly 4 is composed of an Aortic Valve Housing 26 composed of titanium and an Aortic Housing Liner 28 (not shown in FIG. 1) composed of polyester fabric. The Aortic Housing Liner 28 covers the blood contacting internal surfaces of the Aortic Valve Housing 26. A Conduit End Opening 30 of Aortic Valve Housing 26 is sized to accept a Ventricle Conduit 32. A Valve End Opening 34 of Aortic Valve Housing 26 is configured with an Annular Surface 36 (not shown in FIG. 1) to mate with Periphery Surface 22 of Prosthetic Valve 8. The Valve End Opening 34 is larger than the Conduit End Opening 30. Near the Valve End Opening 34, the external surface of the Aortic Valve Housing 26 has External Threads 38.

The larger valve end opening 20 and the smaller conduit end opening 14 of the ventricular valve housing 10 are separated by a transition region having a sloped inner surface of varying internal diameter. Similarly, the larger valve end opening 34 and the smaller conduit end opening 30 of the aortic valve housing 26 are separated by a transition region having a sloped inner surface. As will be appreciated by those skilled in the art, the transition regions of the ventricular valve housing 10 and the aortic valve housing 26 provide a gradual transition between the internal diameters of the valve end openings and the conduit end openings.

The Connecting Locknut 6 is composed of titanium. The Connecting Locknut 6 has a Flange Surface 40 and Internal Threads 42.

The Prosthetic Heart Valve 8 consists of a Leaflet 44, a Frame 46, and the Periphery Surface 22. The Peripheral Surface 22 is composed of polyester fabric.

At the time of implant, the Prosthetic Heart Valve 8 is inserted between the Ventricular Valve Housing 10 and the Aortic Valve Housing 26. In this position, the Periphery Surface 22 of the Prosthetic Heart Valve 8 is in contact with Annular Surface 24 and Annular Surface 36. To maintain this contact and to ensure blood does not flow around the Periphery Surface 22, the Internal Threads 42 of Connecting Locknut 12 are engaged with the External Threads 38 of the Aortic Valve Housing 26 until Flange 21 is closely position against Flange Surface 40 causing the Periphery Surface 22 to be compressed and firmly immobilized between the two valve housings.

Figure 3:
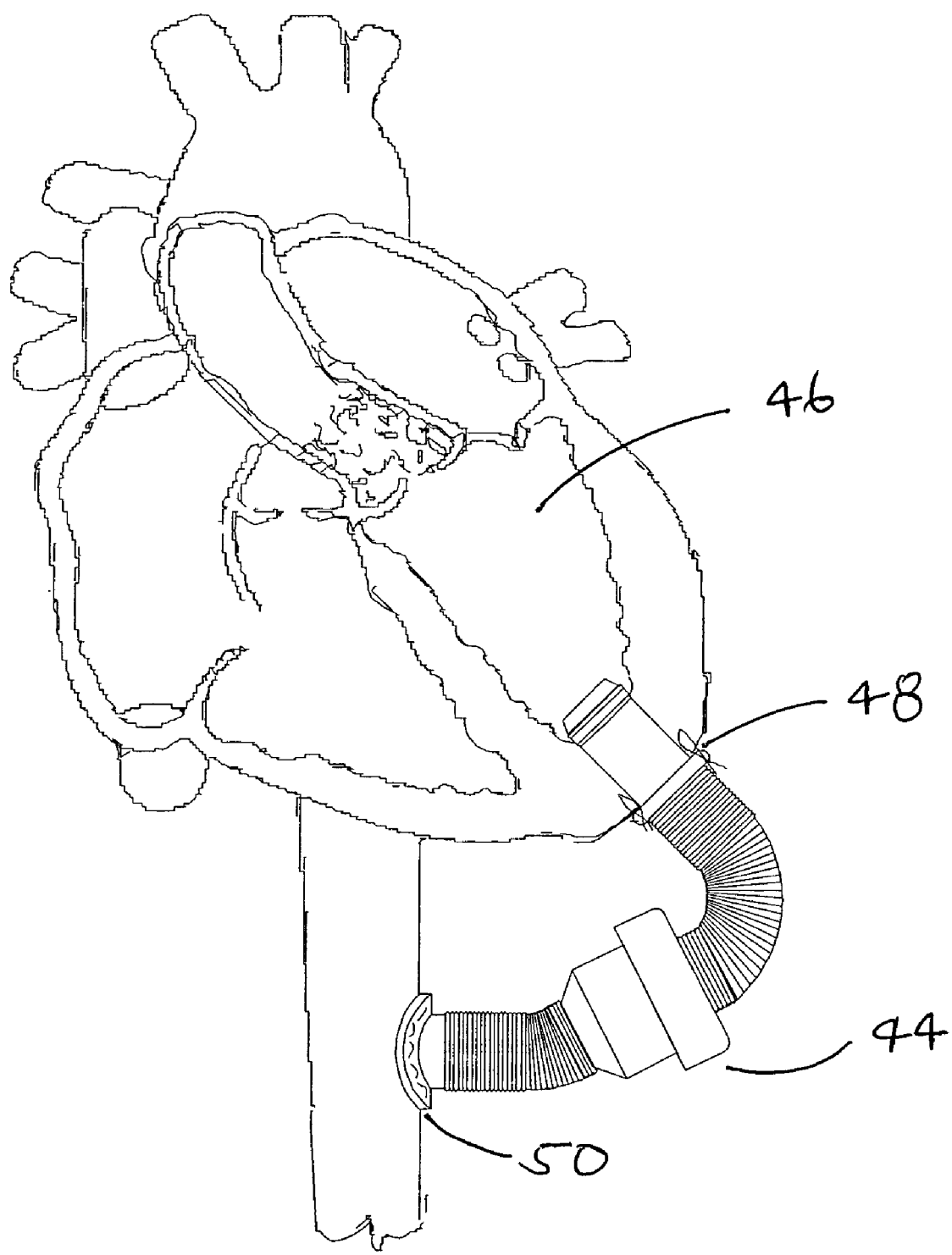
FIG. 3 is a mixed side view/cross section view of the bypass valve graft attached to the ventricle and aorta within a human body.

Shown in FIG. 3 is a preferred embodiment of a Prosthetic Heart Valve Housing 44 installed in a Human Heart 46 between the Apex 48 and the Aorta 50.

Figure 4A:
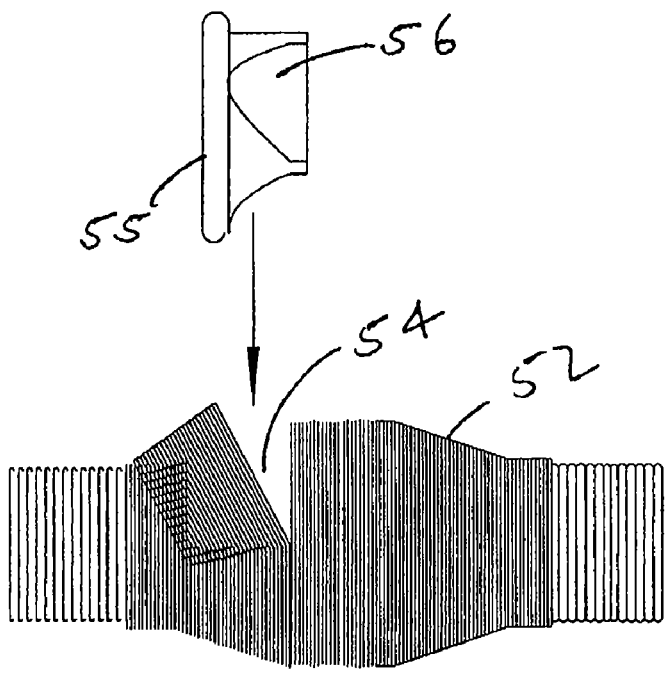
FIGS. 4a-4c illustrate an exemplary alternative embodiment of the present invention wherein an inlet valve housing element and an outlet valve housing element are combined together to form a single heart valve housing unit.
Figure 4B:
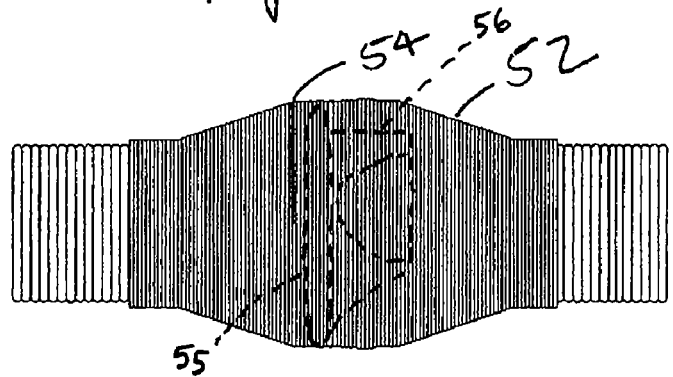
Figure 4C:
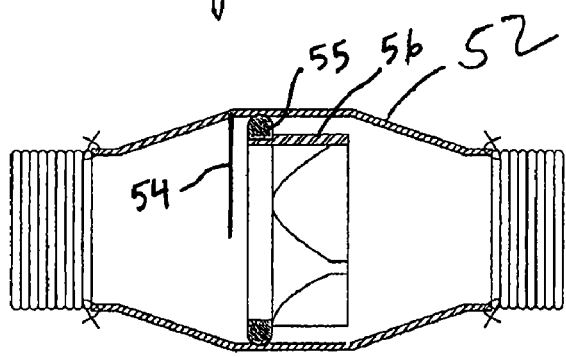

In one embodiment as shown in FIGS. 4a, 4b, and 4c, the outlet and inlet valve housing elements can be combined to form one Valve Housing 52. The Valve Housing 52 is composed of polyester fabric or another suitable biomaterial or combination of biomaterials. A slot or Opening 54 is formed in the Valve Housing 52 to allow a Prosthetic Valve 56 having a Periphery Surface 55 to be inserted and seated into the major internal diameter of the Valve Housing 52. Once inserted, the Opening 54 is closed by suturing, applying adhesive, applying a clip or clamp or some other suitable means to form a blood tight seal preventing blood flow outside of the housing. The Periphery Surface 55 of the Prosthetic Valve 54 is held tightly against the internal surface of the valve housing 52 by employing a preformed annular groove or applying adhesive, sutures, clips or some other suitable fastening means.

Summary, Ramifications, and Scope

The reader will see that the invention, consisting of two implantable devices, when combined with a prosthetic valve, alleviates the prior art problems associated with off-pump apicoaortic procedures.

The invention, when compared to prior art, provides an improved valve bypass graft adopted for use with a prosthetic heart valve that can be installed into the valve bypass graft at the time of implant.

Specifically, the invention has the following advantages:

This invention encourages the use of the most appropriate available prosthetic heart valve by allowing a surgeon, at the time of implantation, to select for installation into the prosthetic heart valve housing a prosthetic heart valve having a proven long term performance history and to install the selected prosthetic valve into the prosthetic heart valve housing without need to alter or modified the valve in anyway.

This invention maximizes blood flow through the implant by allowing a surgeon to use a prosthetic valve that is larger in diameter than the conduits connected to it.

This invention minimizes the risks associated with a subsequent valve replacement procedure by allowing the implanted prosthetic valve to be easily removed and replaced.

This invention simplifies the prosthetic valve installation by eliminating the need for suturing the valve to the adjoining conduits.

This invention simplifies the valve bypass graft procedure by allowing any necessary implantation tools to be inserted and removed though the prosthetic heart valve housing without the need for pre-cut slits through the conduits.

The invention minimizes adverse tissue healing response or adverse blood interaction by providing common blood contacting surface throughout the device.

Although the description above contains many specifications, these should not be construed as limiting the scope of the invention but as merely providing illustrations of the presently preferred embodiment of this invention. For example:

Reference was made throughout the application that the aorta is the specific vessel connection site. Other vessel locations would be just as feasible. Also, other locations in the heart, such as the right ventricle, could be accessed as well, as described in prior art.

Many different valve housing shapes could be employed that could mimic the shape and function of the native aortic root and sinus.

The diameter ratios of conduit size to valve size could range from 1:1 to 1:2 or larger.

The Connecting Locknut component can be removed completely and replaced by joining mechanisms contained in the valve housings.

Thus, the scope of the invention should be determined by the appended claims and their legal equivalents rather than by the examples given.

The invention claimed is:

1. An implantable device for holding a surgeon selected prosthetic heart valve comprising:
   a. a first housing having a first end with a first internal diameter, a second end with a second internal diameter, and a transition region axially spaced between said first and second ends with a varying internal diameter, said second internal diameter being larger than said first internal diameter,
   b. an annular surface extending radially outward from said second end of said first housing having seating means for seating to an annular periphery surface of a prosthetic heart valve,
   c. a second housing having a first end with a first internal diameter, a second end with a second internal diameter, and a transition region axially spaced between said first and second ends with a varying internal diameter, said second internal diameter being larger than said first internal diameter,
   d. an annular surface on said second end of said second housing having seating means for seating to the annular periphery surface of the prosthetic heart valve, and
   e. a connecting member for joining said second end of said first housing with said second end of said second housing, said connector member movable relative to said first and second housings,
   f. wherein said radially extending annular surface of said first housing is receivable within said second end of said second housing when said first and second housings are joined with said connecting member and further wherein said connecting member is structured to compress and immobilize said prosthetic heart valve between said first and second housings.

2. The implantable device of claim 1, the ratio of the cross sectional area of the second end of the first housing to the cross sectional area of the first end of the first housing is greater than 1.2:1.

3. The implantable device of claim 1 wherein the implantable device is configured to regulate flow in a conduit connecting the apex of the left ventricle of the heart to the aorta.

4. The implantable device of claim 1, further comprising a first liner disposed on an inner surface of the first housing and a second liner disposed on an inner surface of a second housing.

5. The implantable device of claim 4, wherein the first and second liners comprise a polyester fabric.

6. The implantable device of claim 1, wherein at least one of said first and second housings are formed of titanium.

7. The implantable device of claim 1, wherein the second housing includes a threaded outer surface adjacent the second end and the connecting member includes a threaded inner surface, the threaded outer surface of the second housing being structured to mate with the threaded inner surface of the connecting member to couple the first housing to the second housing.

\* \* \* \* \*